US008404665B2

(12) United States Patent
Shami

(10) Patent No.: US 8,404,665 B2
(45) Date of Patent: Mar. 26, 2013

(54) IN VIVO USE OF GLUTATHIONE S-TRANSFERASE ACTIVATED NITRIC OXIDE DONORS

(75) Inventor: Paul Shami, Salt Lake City, UT (US)

(73) Assignee: University of Utah Research Foundation

( * ) Notice: Subject to any disclaimer, the term of this patent is extended or adjusted under 35 U.S.C. 154(b) by 334 days.

(21) Appl. No.: 10/508,744

(22) PCT Filed: Mar. 21, 2003

(86) PCT No.: PCT/US03/08877
§ 371 (c)(1),
(2), (4) Date: Sep. 20, 2004

(87) PCT Pub. No.: WO03/080039
PCT Pub. Date: Oct. 2, 2003

(65) Prior Publication Data
US 2005/0171066 A1    Aug. 4, 2005

Related U.S. Application Data

(60) Provisional application No. 60/366,221, filed on Mar. 21, 2002.

(51) Int. Cl.
*A61K 31/655* (2006.01)
*A61K 31/506* (2006.01)
*A61K 31/495* (2006.01)

(52) U.S. Cl. ............. 514/150; 514/255.01; 514/252.141

(58) Field of Classification Search .................. 514/150, 514/561, 149, 42, 255.01, 252.14; 424/78.26
See application file for complete search history.

(56) References Cited

U.S. PATENT DOCUMENTS

| | | | |
|---|---|---|---|
| 4,535,154 A | 8/1985 | Keefer et al. | |
| 4,954,526 A | 9/1990 | Keefer et al. | |
| 4,986,210 A | 1/1991 | Holstein et al. | |
| 5,039,705 A | 8/1991 | Keefer et al. | |
| 5,155,137 A | 10/1992 | Keefer et al. | |
| 5,185,376 A | 2/1993 | Keefer et al. | |
| 5,208,233 A | 5/1993 | Keefer et al. | |
| 5,212,204 A | 5/1993 | Keefer et al. | |
| 5,250,550 A | 10/1993 | Keefer et al. | |
| 5,366,997 A | 11/1994 | Keefer et al. | |
| 5,389,675 A | 2/1995 | Christodoulou et al. | |
| 5,405,919 A | 4/1995 | Keefer et al. | |
| 5,525,357 A | 6/1996 | Keefer et al. | |
| 5,632,981 A | 5/1997 | Saavedra et al. | |
| 5,650,447 A | 7/1997 | Keefer et al. | |
| 5,676,963 A | 10/1997 | Keefer et al. | |
| 5,683,668 A | 11/1997 | Hrabie et al. | |
| 5,700,830 A | 12/1997 | Korthuis et al. | |
| 5,718,892 A | 2/1998 | Keefer et al. | |
| 5,721,365 A | 2/1998 | Keefer et al. | |
| 5,731,305 A | 3/1998 | Keefer et al. | |
| 5,814,656 A | 9/1998 | Saavedra et al. | |
| 5,814,666 A | 9/1998 | Green et al. | |
| 5,910,316 A | 6/1999 | Keefer et al. | |
| 6,057,367 A * | 5/2000 | Stamler et al. ................ | 514/561 |
| 6,110,453 A | 8/2000 | Keefer et al. | |
| 6,200,558 B1 | 3/2001 | Saavedra et al. | |
| 6,232,336 B1 | 5/2001 | Hrabie et al. | |
| 6,265,420 B1 * | 7/2001 | Lai ................................. | 514/310 |
| 6,270,779 B1 | 8/2001 | Fitzhugh et al. | |
| 6,290,981 B1 | 9/2001 | Keefer et al. | |
| 6,379,660 B1 | 4/2002 | Saavedra et al. | |
| 6,511,991 B2 | 1/2003 | Hrabie et al. | |
| 6,887,485 B2 | 5/2005 | Keefer et al. | |
| 2002/0119115 A1 | 8/2002 | Keefer et al. | |
| 2003/0147845 A1 * | 8/2003 | Saavedra et al. ............ | 424/78.26 |

FOREIGN PATENT DOCUMENTS

| WO | WO 93/20806 A1 | 10/1993 |
|---|---|---|
| WO | WO 96/15781 A1 | 5/1996 |
| WO | WO98/13358 * | 2/1998 |
| WO | WO 01/92215 | 12/2001 |

OTHER PUBLICATIONS

Moscow et al., Isolation of the ionic glutathione S-transferase cDNA and the relation of its gene expression to estrogen-receptor content in primary breast cancer PNAS vol. 85:6518-6522, 1988.*
Magrinat et al., Nitric oxide modulation of human leukemia cell differentiation and gene expressionBlood vol. 80:1880-1884, 1992.*
Shami et al, Nitric Oxide modulation of the growth and differentiation of freshly isolated acute non -lymphocytic leukemia cells (leukemia Research vol. 19 527-533, 1995).*
Cui et al. Cancer Research 54, 2462-2467 1994.*
Ferrandina et al., GGT activity in epithelial ovarian cancer. Annals. of Oncology 8, 343-350, 1997.*
Iwamoto et al. Apoptosis 4: (1999) 59-66.*
O'connell et al. The New England J. of Medicine (1994), 502-506).*
Isaacs J. NCI 92(17), 2000).*
Brooks et al. British J. Cancer (1996); 74, 1518-1925.*
Anderson, M. E. (1998) Chem. Biol. Interact. 111-112: 1-14.
Armstrong, R. N. et al. (1994) Adv. Enzymol. Relat. Areas Mol. Biol. 69:1-44.
Armstrong, R. N. et al. (1997) Chem. Res. Toxicol. 10:2-18.
Bico, P. et al. (1994) Biochem. Mol. Biol. Int. 33:837-892.
Brünger, A.T. et al. (1997) "Chrystallographic refinement by simulated annealing: Methods and Applications," Methods Enzymol. 277: 243-269.

(Continued)

Primary Examiner — Shirley V Gembeh
(74) Attorney, Agent, or Firm — Gardner Groff Greenwald & Villanueva, P.C.

(57) ABSTRACT

The present invention provides for a method of simultaneously treating both cancer and the Multidrug Resistance Phenotype via inhibition of cellular thiols, such as Glutathione S-Transferase (GST). This enzyme is overproduced in leukemia and solid tumor cells and is one of the main pathways involved in the Multidrug Resistance phenotype. The treatment provides for the administration of a chemically inert pro-drug, designed to be a specific substrate for the GST enzyme that, once cleaved, liberates the bioactive toxin Nitric Oxide (NO) intracellularly at the site of a malignant growth. NO then acts to inhibit the growth of the malignant cells and to induce cellular differentiation and apoptosis therein, effectively treating an existing cancerous condition. Additionally, once NO is liberated from the pro-drug, the remaining structure acts to inhibit further GST activity, providing a treatment for the Multidrug Resistant phenotype.

16 Claims, No Drawings

OTHER PUBLICATIONS

Cameron, A. D. et al. (1995) Structure 3: 717-727.
Cokic, Vladan P. et al. (2003) "Hydroxyurea induces fetal hemoglobin by the nitric oxide-dependent activation of soluble guanylyl cyclase" *J Clin.Invest.* 111:231-239.
Dirr, H. et al. (1994) Eur. J. Biochem. 220: 645-661.
Engh, R. A. et al. (1991) Acta Crystallogr. 47:392-400.
Habig, W. H. (1974) Journal of Biochemistry, 249: 7130-7139.
Hayes, J. D. et al (1995) Crit. Rev. Biochem. Mol. Biol. 30: 445-600.
Ji, X. et al. (1993) Biochemistry 32:12949-12954.
Jia, L. et al. (1993) *J. Pharmnacol Exp Ther* 267: 371-378.
Jones, T. A. et al. (1997) "Electron-density map interpretation," Methods Enzymol. 277: 173-208.
Keefer, L. K. et al. (1996) Methods Enzymol. 268: 281-293).
Magrinat, G. et al (1992) Blood 80: 1880-1884.
Mancini, I. et al. (1998) Tetrahedron Letters 39: 1611-1614.
Martin W. et al., (1985) "Blockade of endothelium-dependent and glyceryl trinitrate-induced relaxation of rabbit aorta by certain ferrous hemoproteins," J Pharmacol Exp Ther 233:679-685.
Monga, M. et al. (2002) Leukemia 16(4) 520-526.
Monks A. et al. (1991) "Feasibility of a high-flux anticancer drug screen using a diverse panel of cultured human tumor cell lines," J Natl Cancer Inst. 83: 757-766.
Moscow, Jeffrey A. et al. "Isolation of the Human Anionic Glutathione S-Transferase cDNA and the Relation of Its Gene Expression to Estrogen-Receptor Content in Primary Breast Cancer," *Proceedings of the National Academy of Sciences of the U.S.A.*, vol. 85, No. 17 (Sep. 1, 1988), pp. 6518-6522.
Nicoletti, I. et al.. (1991) J. Immunol. Methods 139: 271-279.
Powell, M. J. D. (1977), "Restart Procedures for the Conjugate Gradient Method," Mathematical Programming 12:241-254.
Prade, L. et al. (1997) Structure 5: 1287-1295.
Remington, J.P. "Remington's Pharmaceutical Sciences" $15^{th}$ Ed., Ch. 33, pp. 624-652, 1035-1038 and 1570-1580. Mack Publishing Co. 1975.
Saavedra, J. E. et al(2001) "Journal of Organic Chemistry," 66:3090-3098.
Saavedra, J. E. et al (1999) "Journal of Organic Chemistry," 64:5124-5131.
Shami, Paul J. et al., (1995) "Nitric Oxide Modulation of the Growth and Differentiation of Freshly Isolated Acute Non-Lymphocytic Leukemia Cells," *Leukemia Research* vol. 19, No. 8, pp. 527-533.
Shami, P. J. et al (1998) Leukemia 12: 1461-1466.
Shami, Paul J. et al. (Apr. 2003) "JS-K, $O^2$-(2,4-Dinitrophenyl) 1-[(4-ethoxycarbonyl)piperazin-1-yl]diazen-1-ium-1,2-diolate, a Glutathione/Glutathione S-Transferase-activated Nitric Oxide Donor of the Diazeniumdiolate Class with Potent Antineoplastic Activity[1]", Molecular Cancer Therapeutics, vol. 2, 1-9.
Sinning, I., et al. (1993) J. Mol. Biol. 232:192-212.
Wilce, M. C. J. et al. (1994) Biochem. Biophys. Acta12505: 1-18.
Office Action dated Apr. 24, 2009 for European application No. 03723806.0-1216.
Office Action dated Feb. 18, 2011 for European application No. 03723806.0-1216.
Response to Office Action dated Aug. 20, 2009 for European application No. 03723806.0-1216.
"Blood", Journal of the American Society of Hematology, Dec. 2000, Abstract, vol. 96, No. 11, Part 1 of 2, 308a, California.
Shami et al. "In vivo antileukemic activity of 'JK-K' in NOD-SCID mice", American Association for Cancer Research, Mar. 2002, Abstract.

* cited by examiner

IN VIVO USE OF GLUTATHIONE S-TRANSFERASE ACTIVATED NITRIC OXIDE DONORS

CROSS REFERENCE TO RELATED APPLICATIONS

This application claims priority from U.S. Provisional Patent Application No. 60/366,221 filed Mar. 21, 2002.

ACKNOWLEDGMENT OF FEDERAL RESEARCH SUPPORT

The U.S. Government has certain rights in the invention based upon partial support by National Institute of Environmental Health Sciences Grant ES09140.

BACKGROUND OF THE INVENTION

Nitric oxide (NO) is integral to many biological processes including the control of blood pressure, protection against microbial infection and neurotransmission. Additionally, it appears to be a potent cytotoxin to tumor cells. Among its mechanisms of action on malignant cells, nitric oxide appears to inhibit DNA synthesis and mitochondrial respiration in vitro. It induces programmed cell death or apoptosis in these cells.

Unfortunately, NO itself is difficult to administer as it is a highly reactive gas. It also causes hypotension if administered systemically. These limitations have prevented its use to date as an antineoplastic agent.

Several attempts have been made to formulate a pharmaceutical containing NO in the form of a prodrug. This method has not been successful as the prodrugs created to date are cleaved by ubiquitously available enzymes resulting in systemic release of NO. This causes hypotension and precludes the ability of these compounds to be used as therapeutics.

Methods of delivering NO directly to a specific cell type, such as a cancer cell, are needed that are capable of delivery without systemic release of NO.

SUMMARY OF THE INVENTION

A method for the specific delivery of NO to a cell is provided by the present invention, including a methodology for the treatment or prevention for cancer. Any cell containing Glutathione S-Transferase (GST) can be targeted and modified by the method of the present invention. Malignant cells of different tissue origin overexpress GST as compared to their normal counterpart thus allowing for the selective delivery of NO while sparing normal cells.

In certain embodiments, the methods comprise contacting a cancer cell having endogenous Glutathione S-Transferase (GST) with an $O^2$-aryl diazeniumdiolate compound. In a particular embodiment, the GST cleaves the $O^2$-aryl diazeniumdiolate compound to generate an activated $O^2$-aryl diazeniumdiolate compound and release of nitric oxide (NO). Such activated $O^2$-aryl diazeniumdiolate compounds inhibit GST activity. In a particular embodiment the activated $O^2$-aryl diazeniumdiolate compound is $O^2$-(2,4-dinitrophenyl) 1-[(4-ethoxycarbonyl)piperazin-1-yl]diazen-1-ium-1,2-diolate (JS-K) which generates the activated $O^2$-aryl diazeniumdiolate compound 1-[(4-ethoxycarbonyl)piperazin-1-yl]diazen-1-ium-1,2-diolate. In another embodiment, the $O^2$-aryl diazeniumdiolate compound is $O^2$-(2,4-dinitrophenyl) 1-[4-phenylpiperazin-1-yl]diazen-1-ium-1,2-diolate (JXC-2-40) which generates the activated $O^2$-aryl diazeniumdiolate compound 1-[4-phenylpiperazin-1-yl]diazen-1-ium-1,2-diolate. In another embodiment, the $O^2$-aryl diazeniumdiolate compound is $O^2$-(2,4-dinitrophenyl) 1-[4-pyrimidin-2-yl]piperazin-1-yl]diazen-1-ium-1,2-diolate and the activated $O^2$-aryl diazeniumdiolate compound is 1-[4-pyrimidin-2-yl]piperazin-1-yl]diazen-1-ium-1,2-diolate (JXC-2-56). Such NO may inhibit cancer growth or induce apoptosis or cell differentiation.

In another embodiment, the methods of the present invention are utilized to treat cancer by contacting a cancer cell having endogenous GST with an $O^2$-aryl diazeniumdiolate compound that is cleaved in the presence of GST to generate NO and an activated $O^2$-aryl diazeniumdiolate compound; where the activated $O^2$-aryl diazeniumdiolate compound inhibits GST activity and NO has any of the following activities; inhibiting cancer cell growth, inducing apoptosis and inducing cell differentiation.

In another embodiment, the present invention is utilized to treat an infection comprising contacting an infectious cell having endogenous GST with an $O^2$-aryl diazeniumdiolate compound. In a particular embodiment, the GST cleaves the $O^2$-aryl diazeniumdiolate compound to generate an activated $O^2$-aryl diazeniumdiolate compound and release nitric oxide (NO). Such activated $O^2$-aryl diazeniumdiolate compound can inhibit GST activity. Such NO can inhibit cell growth. In a particular embodiment, the infection is bacterial, viral, fungal or parasitic.

In certain embodiments, the present invention is utilized to prevent cancer by administering an $O^2$-aryl diazeniumdiolate compound to the individual. Such $O^2$-aryl diazeniumdiolate compound may inhibit the ability of a cancer cell to implant.

In another embodiment, the present invention is utilized to kill a target cell having endogenous GST comprising contacting said cell with an $O^2$-aryl diazeniumdiolate compound. Such GST may cleave the $O^2$-aryl diazeniumdiolate compound to generate an activated $O^2$-aryl diazeniumdiolate compound and release of nitric oxide (NO). Such activated $O^2$-aryl diazeniumdiolate may inhibit GST activity. A target cell can include a cancer cell. Such NO may inhibit cancer cell growth or induce cell differentiation or apoptosis. Administration of such $O^2$-aryl diazeniumdiolate compound does not induce hypotension in an individual.

Methods of the present invention may further provide for administration of an agent selected from the group consisting of a chemotherapeutic agent and a nitric oxide scavenger. Such chemotherapeutic may be selected from the group consisting of, but not limited to, adriamycin; 5-fluorouracil (5FU); etoposide (VP-16); camptothecin; actinomycin-D; mitomycin C; cisplatin (CDDP); hydrogen peroxide; a DNA damaging agent, such as X-rays or radiation and a combination of any of the above. Such nitric oxide scavenger may be selected from the group consisting of, but not limited to, non-heme iron-containing peptides or proteins, porphyrins, metalloporphyrins, dimercaptosuccinic acid, phenanthroline, desferrioxamine, pyridoxal isonicotinoyl hydrazone (PIH), 1,2-dimethyl-3-hydroxypyrid-4-one (L1), [+]1,2-bis(3,5-dioxopiperazine-1-yl)propane (ICRF-187), 2-mercaptonicotinic acid, nitronyl nitroxide, nitric oxide chelotropes (e.g., compounds containing the 7,7,8,8-tetraalkyl-O-quinodimethane type moiety), 2-phenyl-4,4,5,5-tetramethylimidazoline-1-oxyl 3-oxide (PTIO), carboxy-PTIO, phenyl-n-tert-butyl nitrone, and combinations of two or more thereof.

Methods of the present invention utilize $O^2$-aryl diazeniumdiolate compounds. Such compounds may be selected from the group consisting of, but not limited to, $O^2$-(2,4-dinitrophenyl) 1-[(4-ethoxycarbonyl)piperazin-1-yl]diazen-1-ium-1,2-diolate (JS-K), $O^2$-(2,4-dinitrophenyl) 1-[4-phenylpiperazin-1-yl]diazen-1-ium-1,2-diolate (JXC-2-40) and $O^2$-(2,4-dinitrophenyl) 1-[4-pyrimidin-2-yl]diazen-1-ium-1, 2-diolate (JXC-2-56).

Methods of the present invention further provide for delivery of NO directly to a cell with high levels of GST without induction of hypotension.

Many alterations and variations of the invention exist as described herein. The invention is exemplified for JS-K in cancer cells but is applicable to any cell type or organism. The present invention can apply to any of the following cells, although the methods are not limited to the cells or organisms herein listed: prostate, leukemia, renal, melanoma, colon, ovarian, lung, central nervous system or breast cancer cell. The elements necessary to carry out the methods of the present invention as herein disclosed can be adapted for application in any cell or organism. The invention therefore provides a general method for delivering NO to any cell or organism with high levels of endogenous GST.

DETAILED DESCRIPTION OF THE INVENTION

The present invention relates to methods of delivering NO to cells containing high levels of GST. Malignant cells of different tissue origin overexpress GST as compared to their normal counterpart thus allowing for the selective delivery of NO while sparing normal cells. In contrast to previously known methods of delivering NO, the present invention delivers NO directly to a cell rather than causing systemic exposure to NO that results in hypotension. Any cell or organism containing GST may be targeted for delivery of NO by the methods of the present invention. The methods provide both a treatment and preventative methodology for cancer. The methods of the present invention also provide a method of treating an infection such as a parasitic, viral, bacterial or fungal infection. The methods also provide a mechanism to kill a cell.

DEFINITIONS

For the purposes of the present invention, the following terms shall have the following meanings:

As used herein, the term "apoptosis" refers to programmed cell death. In such programmed cell death, cells have characteristics that may include, but are not limited to, cellular shrinkage, mitochondrial break-down, nuclear chromatin breakdown and exposure of the cell membrane phospholipid phosphatidylserine.

As used herein, the term "differentiation" refers to any change in the cell due to administration of NO. Such change may include, but is not limited to, development of folded nuclei, large cytoplasms and cytoplasmic vacuoles or assuming any phenotypic features of normal cells. In some instances, differentiation may be detectable with non-specific esterase staining.

As used herein, the term "hypotension" refers to an abnormal condition in which the blood pressure is lower than 90/60 or is low enough to cause symptoms or interfere with well-being.

As used herein, the term "cell growth" refers to an addition in cell number, which may be measured, for example, by volume or cell number.

As used herein, the term "$O^2$-aryl diazeniumdiolate compound" refers to a class of compounds consisting of arylated diazeniumdiolates designed to be activated for NO release by reaction with cellular thiols, such as glutathione (GSH), with or without catalysis by Glutathione S-Transferase (GST).

As used herein, the term "Glutathione S-Transferase (GST)" refers to all isoforms of GST, including but not limited to, the Alpha ($\alpha$), Mu ($\mu$) and pi ($\pi$) isoforms of GST.

In the present invention, the term "activated $O^2$-aryl diazeniumdiolate compound" refers to the portion of the $O^2$-aryl diazeniumdiolate compound that remains after NO is cleaved from it. Such activated $O^2$-aryl diazeniumdiolate compound may consist of an aryl ring designed to inhibit GSTs.

As used herein, the term "Multidrug Resistance" (MDR) phenotype is a cell's resistance to a xenobiotic, such as an anticancer drug. It encompasses any strategy employed by a tumor cell to evade the toxic effect of a xenobiotic agent. It is characterized by a decreased sensitivity of a tumor cell not only to the xenobiotic agent, but also to a broad spectrum of drugs with neither structural homology nor common targets.

As used herein, the term "xenobiotic" refers to any foreign compound including naturally present compounds administered by alternate routes or at unnatural concentrations. Such compounds include, but are not limited to, chemotherapeutic agents.

As used in the present invention, the term "individual" refers to any organism, including but not limited to a mammal; such as a human or an animal of either gender; an insect; a parasite; a virus; a bacteria or a fungi.

As used in the present invention, the term "nitric oxide scavenger" refers to any compound or composition that removes nitric oxide from a system.

Moreover, for the purposes of the present invention, the term "a" or "an" entity refers to one or more than one of that entity; for example, "a glutathione" or "an JS-K molecule" refers to one or more of those compounds, or at least one compound. As such, the terms "a" or "an", "one or more" and "at least one" can be used interchangeably herein. It is also to be noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated or biologically pure compound is a compound that has been removed from its natural milieu. As such, "isolated" and "biologically pure" do not necessarily reflect the extent to which the compound has been purified. An isolated compound of the present invention can be obtained from its natural source or produced using molecular biology techniques or chemical synthesis.

Compounds

An $O^2$-aryl diazeniumdiolate compound of the present invention includes at least one NO molecule and an activated $O^2$-aryl diazeniumdiolate compound upon reaction with an endogenous cellular thiol. In a particular embodiment, such cellular thiol is Glutathione S-Transferase (GST). An activated $O^2$-aryl diazeniumdiolate compound of the present invention inhibits the MDR phenotype. At least one NO molecule of the present invention inhibits cell growth and induces cell differentiation and apoptosis.

An $O^2$-aryl diazeniumdiolate compound as herein described releases at least one NO molecule. In a preferred embodiment a $O^2$-aryl diazeniumdiolate compound would have at least two NO molecules in order to inhibit cell growth and induce cell differentiation and apoptosis. An $O^2$-aryl diazeniumdiolate compound having more than two NO molecules is within the scope of the invention. An $O^2$-aryl diazeniumdiolate compound having more than two NO molecules would have progressively greater effect on cell growth, differentiation and apoptosis.

While the $O^2$-aryl diazeniumdiolate compounds of the present invention are capable of releasing NO, such compounds preferably release NO under physiological conditions. The rate at which the compounds utilized in the methods of the present invention release nitric oxide is dependent on at least pH and temperature. The compound's effect on cell proliferation, differentiation and apoptosis, as well as on the MDR phenotype, can be controlled by appropriate selection of these conditions.

The $O^2$-aryl diazeniumdiolate compound of the present invention can be any $O^2$-aryl diazeniumdiolate compound capable of releasing NO when reacted with a cellular thiol, such as GST. In a particular embodiment, the $O^2$-aryl diazeniumdiolate compound is $O^2$-(2,4-dinitrophenyl) 1-[(4-ethoxycarbonyl)piperazin-1-yl]diazen-1-ium-1,2-diolate (JS-K). In an alternative embodiment, the $O^2$-aryl diazeniumdiolate compound is $O^2$-(2,4-dinitrophenyl) 1-[4-phenylpiperazin-1-yl]diazen-1-ium-1,2-diolate (JXC-2-40). In another alternative embodiment, the $O^2$-aryl diazeniumdiolate compound is $O^2$-(2,4-dinitrophenyl) 1-[4-(pyrimidin-2-yl)piperazin-1-yl]diazen-1-ium-1,2-diolate (JXC-2-56).

The cellular thiol of the present invention can be any thiol present within a cell. In a particular embodiment, the cellular thiol comprises Glutathione S-Transferase (GST). Such GST may include, but is not limited to, the Alpha ($\alpha$), Mu ($\mu$) and pi ($\pi$) isoforms of GST.

Reaction of the $O^2$-aryl diazeniumdiolate compound with a cellular thiol produces NO and an activated $O^2$-aryl diazeniumdiolate compound. In a particular embodiment, when such $O^2$-aryl diazeniumdiolate compound is JS-K, the activated $O^2$-aryl diazeniumdiolate compound is 1-[(4-ethoxycarbonyl)piperazin-1-yl]diazen-1-ium-1,2-diolate. In another embodiment, when such $O^2$-aryl diazeniumdiolate compound is JXC-2-40, the activated $O^2$-aryl diazeniumdiolate compound is 1-[4-phenylpiperazin-1-yl]diazen-1-ium-1,2-diolate. In another embodiment, when such $O^2$-aryl diazeniumdiolate compound is JXC-2-56, the activated $O^2$-aryl diazeniumdiolate compound is 1-[4-(pyrimidin-2-yl)piperazin-1-yl]diazen-1-ium-1,2-diolate.

The activated $O^2$-aryl diazeniumdiolate compound inhibits the MDR phenotype. In another particular embodiment, the activated $O^2$-aryl diazeniumdiolate compound inhibits the GST pathway. In an alternative embodiment, the activated $O^2$-aryl diazeniumdiolate compound inhibits GST.

The NO of the present invention effects change in the cell. In a particular embodiment, the NO inhibits cell growth. In an alternative embodiment, the NO induces cell differentiation. In another alternative embodiment, the NO induces apoptosis.

The effect of the methods of the present invention on cells can be reversible by the addition of a compound capable of removing or scavenging NO by complexing or reacting with NO in order to counteract the inhibitory effect of the compound of the present invention. The methods of the present invention can therefore be further controlled by use of such a nitric oxide scavenger compound in an appropriate quantity.

In addition to the above-recited compounds, pharmaceutically acceptable salts, zwitterions, and derivatives thereof are also useful in the context of the present invention.

The skilled artisan will realize that the compounds listed above are exemplary only and that many variations may be used, depending on the particular $O^2$-aryl diazeniumdiolate compound.

Treatment of the Multidrug Resistance (MDR) Phenotype

MDR is one of the main impediments to the successful treatment of neoplastic disease. The MDR phenotype is greatly influenced by the Glutathione (GSH) pathway. Glutathione itself is synthesized in a two-step mechanism by the enzymes $\gamma$-glutamyl synthetase ($\gamma$-GCS) and Glutathione synthetase (GS). In an individual with cancer receiving a xenobiotic, such as a chemotherapeutic agent, conjugates can be made consisting of Glutathione (GSH) and such xenobiotic via Glutathione S-Transferase (GST). These conjugates are then pumped out of the cell via the Multidrug Resistance Protein complex (MRP1/MRP2) rendering the xenobiotic ineffective on the cell. In many cancer cells, GST is elevated making the production of conjugates and their transfer out of a cell highly likely.

The methods of the present invention include the inhibition of the MDR phenotype. In a particular embodiment, such inhibition is via administration of an $O^2$-aryl diazeniumdiolate compound. Such compound is inert until activation with a cellular thiol, such as GST, which results in the release of at least one NO molecule and an activated $O^2$-aryl diazeniumdiolate compound. The activated $O^2$-aryl diazeniumdiolate compound acts to inhibit the MDR phenotype. In a particular embodiment, the activated $O^2$-aryl diazeniumdiolate compound inhibits the GST pathway. In another embodiment, the activated $O^2$-aryl diazeniumdiolate compound inhibits GST. The inactivation of GST or the GST pathway results in inhibition of the MDR phenotype allowing a xenobiotic to remain in a cell and exert its effect.

Nitric Oxide Scavenger

Nitric oxide scavengers bind nitric oxide in vivo and the resulting complexes render nitric oxide harmless. The resulting complexes are eventually excreted in the urine of the host. Nitric oxide scavengers are thus used to lower the level of nitric oxide in the subject, for example to a physiologically acceptable level. This may be useful in the context of the present invention in order to decrease NO released from a $O^2$-aryl diazeniumdiolate compound after activation by a cellular thiol, such as GST.

Such nitric oxide scavenger may be selected from the group consisting of, but not limited to, non-heme iron-containing peptides or proteins, porphyrins, metalloporphyrins, dimercaptosuccinic acid, phenanthroline, desferrioxamine, pyridoxal isonicotinoyl hydrazone (PIH), 1,2-dimethyl-3-hydroxypyrid-4-one (L1), [+]1,2-bis(3,5-dioxopiperazine-1-yl) propane (ICRF-187), 2-mercaptonicotinic acid, nitronyl nitroxide, nitric oxide chelotropes (e.g., compounds containing the 7,7,8,8-tetraalkyl-O-quinodimethane type moiety), 2-phenyl-4,4,5,5-tetramethylimidazoline-1-oxyl 3-oxide (PTIO), carboxy-PTIO, phenyl-n-tert-butyl nitrone, and combinations of two or more thereof. Additionally, such nitric oxide scavenger may be selected from the group consisting of but not limited to nitrone derivatives; a dithiocarbamate-containing molecule; and a vitamin B12 molecule, such as hydroxocobalamin or derivatives thereof.

Such nitric oxide scavenger may be delivered in a time release delivery vehicle that substantially delays release of the scavenger for a sufficient amount of time after administration of the $O^2$-aryl diazeniumdiolate compound to a subject in need thereof that the nitric oxide source achieves a beneficial effect prior to the release of the scavenger. In a particular embodiment, the nitric oxide scavenger is contained in a pharmaceutically acceptable carrier therefore, optionally contained within a time release vehicle.

The nitric oxide scavengers used in the inventive method chemically bind free nitric oxide in the blood stream and tissues and are administered in sufficient amount to lower the level of nitric oxide in the subject to a physiologically acceptable level.

Treatment of Cancer

Tumor cell resistance to chemotherapeutic agents represents a major problem in clinical oncology. One goal of current cancer research is to find ways to improve the efficacy of chemo- and radiotherapy. One way is by combining such traditional therapies with other agents. In the context of the present invention, it is contemplated that therapy with an $O^2$-aryl diazeniumdiolate compound could be used similarly in conjunction with chemo- or radiotherapeutic intervention. The $O^2$-aryl diazeniumdiolate compound can be selected from the group consisting of but not limited to JS-K. This treatment option may offer a combinatorial therapeutic effect along with the DNA damaging agent. Different cancer therapeutic agents and methods of treatment utilizing such agents are well-known in the art.

In order to inhibit cell growth, induce cell differentiation, induce apoptosis, inhibit MDR phenotype, inhibit metastasis, inhibit angiogenesis or otherwise reverse or reduce the malignant phenotype of tumor cells using the methods and compositions of the present invention, one would generally contact a "target" cell with an $O^2$-aryl diazeniumdiolate compound. In a particular embodiment of the present invention, such $O^2$-aryl diazeniumdiolate compound is JS-K. In another embodiment, such $O^2$-aryl diazeniumdiolate compound is $O^2$-(2,4-dinitrophenyl) 1-[4-phenylpiperazin-1-yl]diazen-1-ium-1,2-diolate (JXC-2-40). In a third embodiment, such $O^2$-aryl diazeniumdiolate compound is $O^2$-(2,4-dinitrophenyl) 1-[4-pyrimidin-2-yl]diazen-1-ium-1,2-diolate (JXC-2-56). In an alternative embodiment, an $O^2$-aryl diazeniumdiolate compound and at least one other agent is administered. In a particular embodiment, the additional agent is a chemotherapeutic agent. In another embodiment, the additional agent is a nitric oxide scavenger. These compositions can be provided in a combined amount effective to kill or inhibit proliferation of the cell. This process may involve contacting the cells with the $O^2$-aryl diazeniumdiolate compound or the $O^2$-aryl diazeniumdiolate compound and the agent(s) or factor(s) at the same time. This may be achieved by contacting the cell with a single composition or pharmacological formulation that includes both agents, or by contacting the cell with two distinct compositions or formulations simultaneously, wherein one composition includes the $O^2$-aryl diazeniumdiolate compound and the other includes the agent.

Alternatively, any of the $O^2$-aryl diazeniumdiolate compound treatments may precede or follow the other agent treatment by intervals ranging from minutes to weeks. In embodiments where the other agent and any of the $O^2$-aryl diazeniumdiolate compounds are applied separately to the cell, one would generally ensure that a significant period of time did not expire between the time of each delivery, such that the agent and $O^2$-aryl diazeniumdiolate compound and/or derivative compounds would still be able to exert an advantageously combined (e.g., synergistic) effect on the cell. In such instances, it is contemplated that one would contact the cell with both modalities within about 12-24 h of each other and, more preferably, within about 6-12 h of each other, with a delay time of only about 12 h being most preferred. In some situations, it may be desirable to extend the duration of treatment with just the therapeutic agent, for example, where several days (2, 3, 4, 5, 6 or 7) to several weeks (1, 2, 3, 4, 5, 6, 7 or 8) lapse between the respective administrations.

To achieve cell killing or to inhibit cell growth, one or both agents are delivered to a cell in an amount effective to kill the cell or inhibit growth.

Agents or factors suitable for use in a combined therapy are any chemical compound or treatment method that induces DNA damage when applied to a cell. Such agents and factors include radiation and waves that induce DNA damage such as γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

In treating cancer according to the invention, one would contact the tumor cells with an $O^2$-aryl diazeniumdiolate compound or an $O^2$-aryl diazeniumdiolate compound and an agent. An additional agent may be delivered by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, or mitomycin C. The agent may be prepared and used as a combined therapeutic composition, or kit, by combining it with an $O^2$-aryl diazeniumdiolate compound, or a derivative compound of an $O^2$-aryl diazeniumdiolate compound, as described above.

Agents that directly cross-link nucleic acids, specifically DNA, are envisaged to facilitate DNA damage leading to a synergistic, antineoplastic combination. Agents such as cisplatin, and other DNA alkylating agents may be used.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered intravenously through bolus injections at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of nucleic acid precursors and subunits also lead to DNA damage. A number of nucleic acid precursors have been developed for this purpose. Particularly useful are agents that have undergone extensive testing and are readily available, such as 5-fluorouracil (5FU). Although quite toxic, 5-FU is applicable in a wide range of carriers, including topical. However intravenous administration with doses ranging from 3 to 15 mg/kg/day is commonly used.

Other DNA-disruptive factors that have been used extensively include γ-rays, X-rays, and/or the directed delivery of radioisotopes to tumor cells. Other forms of DNA damaging factors also are contemplated such as microwaves and UV-irradiation. It is most likely that all of these factors effect a broad range of damage to DNA, on the precursors of DNA, the replication and repair of DNA, and the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, and in particular to pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA and other regulatory agency standards.

Regional delivery of an $O^2$-aryl diazeniumdiolate compound will be a very efficient method for delivering a therapeutically effective dose of the $O^2$-aryl diazeniumdiolate compound to counteract the clinical disease. Similarly, chemo- or radiotherapy may be directed to a particular affected region of the subject's body. Alternatively, systemic delivery of an $O^2$-aryl diazeniumdiolate compound or derivative molecules and/or the agent may be appropriate in certain circumstances, for example, where extensive metastasis has occurred.

Treatment of Other Indications

The methods of the present invention are also of use for the treatment of a parasitic, bacterial, viral or fungal infection in an individual. Such individuals may be treated as described herein. Additionally, the methods are of use in any health condition in an individual where inhibition of cell growth, induction of cell differentiation, induction of apoptosis or inhibition of the MDR phenotype is desirable.

Dosage

The dose administered to an individual in the context of the present invention should be sufficient to effect a therapeutic response in the individual over a reasonable time frame. The dose will be determined by the strength of the particular compound employed and the condition of the individual, as well as the body weight of the individual to be treated. The size of the dose will also be determined by the existence, nature and extent of any adverse side-effects that might accompany the administration of a particular compound.

The extent of desired inhibition of cell growth, inducement of cell differentiation, induction of apoptosis and inhibition of the MDR phenotype will depend on the particular condition or disease being treated, as well as the stability of the patient and possible side-effects. In proper doses and with suitable administration of $O^2$-aryl diazeniumdiolate compounds, the present invention provides for a wide range of the rate of each of these desired effects (inhibition of cell growth, induction of cell differentiation, induction of apoptosis and inhibition of MDR phenotype).

Pharmaceutical Compositions and Routes of Administration

One skilled in the art will appreciate that suitable methods administering a $O^2$-aryl diazeniumdiolate compound to an individual are available, and, although more than one route can be used to administer a particular compound, a particular route can provide a more immediate and more effective reaction than another route. Pharmaceutically acceptable carriers are also well-known to those skilled in the art. The choice of carrier will be determined in part by the particular compound, as well as by the particular method used to administer the composition. Accordingly, there is a wide variety of suitable formulations of the pharmaceutical compositions to be used in the methods of the present invention.

Aqueous compositions of the present invention comprise an effective amount of an $O^2$-aryl diazeniumdiolate compound or derivative molecules, dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

Aqueous compositions of the present invention comprise an effective amount of the compound, dissolved or dispersed in a pharmaceutically acceptable carrier or aqueous medium. Such compositions can also be referred to as inocula. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA and other regulatory agency standards.

The active compounds will generally be formulated for parenteral administration, e.g., formulated for injection via the intravenous, intramuscular, sub-cutaneous, intralesional, or even intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid. It must be stable under the conditions of manufacture and storage and must be preserved against the contaminating action of microorganisms, such as bacteria and fungi.

Solutions of the active compounds can be prepared in water suitably mixed with a surfactant, such as hydroxypropylcellulose. Dispersions can also be prepared in glycerol, liquid polyethylene glycols, and mixtures thereof, and in oils. Under ordinary conditions of storage and use, these preparations contain a preservative to prevent the growth of microorganisms.

The carrier can also be a solvent or dispersion medium containing, for example, water, ethanol, polyol (for example, glycerol, propylene glycol, liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. In the case of microparticles, an aqueous suspending medium may optionally contain a viscosity enhancer such as sodium carboxymethylcellulose and optionally a surfactant such as Tween-20. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580).

The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. The person responsible for administration will, in any event, determine the appropriate dose for the individual subject.

The active therapeutic agents may be formulated within a mixture to comprise about 0.0001 to 1.0 milligrams, or about 0.001 to 0.1 milligrams, or about 1.0 to 100 milligrams or even about 0.01 to 1.0 grams per dose or so. Multiple doses can also be administered.

In addition to the compounds formulated for parenteral administration, such as intravenous or intramuscular injection, other alternative methods of administration of the present invention may also be used, including but not limited to intradermal administration, pulmonary, buccal administration, transdermal administration, and transmucosal administration. All such methods of administration are well known in the art.

One may also use intranasal administration of the present invention, such as with nasal solutions or sprays, aerosols or inhalants. The $O^2$-aryl diazeniumdiolate compounds, alone or in combination with other suitable components, can be made into aerosol formulations to be administered via inhalation. These aerosol formulations can be placed into pressurized acceptable propellants, such as dichlorodifluoromethane, propane, nitrogen, and the like. Additionally, nasal solutions may be utilized in the methods of the present invention and are usually aqueous solutions designed to be administered to the nasal passages in drops or sprays. Nasal solutions are prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and include, for example, antibiotics and antihistamines and are used for asthma prophylaxis.

Additional formulations which are suitable for other modes of administration include suppositories and pessaries. A rectal pessary or suppository may also be used. Suppositories are solid dosage forms of various weights and shapes, usually medicated, for insertion into the rectum or the urethra. After insertion, suppositories soften, melt or dissolve in the cavity fluids. For suppositories, traditional binders and carriers generally include, for example, polyalkylene glycols or triglycerides; such suppositories may be formed from mixtures containing the active ingredient in the range of 0.5% to 10%, preferably 1%-2%.

Oral formulations containing an $O^2$-aryl diazeniumdiolate compound or derivative molecules include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will comprise an inert diluent or assimilable edible carrier, or they may be enclosed in a hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent, methyl and propylparabens as preservatives, a dye and flavoring, such as cherry or orange flavor.

In addition, alternative suitable compositions of the present invention may be used, including but not limited to hydrogels, vaginal rings, patches, crystals, gels, liposomes, microspheres, nanospheres, implants and any other long-term sustained release formulations. All such compositions are well known in the art.

Formulations of use in the methods of the present invention can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Reagents and Statistical Analysis for All Experiments

Chemicals. JS-K (Saavedra, J. E. et al. (2001) Journal of Organic Chemistry 66: 3090-3098) and 4-carbethoxy-PIPERAZI/NO (Saavedra, J. E. et al. (1999) Journal of Organic Chemistry 64: 5124-5131) were synthesized as previously described. S-(2,4-Dinitrophenyl)glutathione was prepared by the method of Mancini et al. (Mancini, I. et al. (1998) Tetrahedron Letters 39: 1611-1614). The pan-caspase inhibitor Z-VAD-FMK was purchased from Biomol (Plymouth Meeting, Pa.). Daunorubicin and etoposide were from Dr. Grayden Harker (University of Utah, Salt Lake City, Utah). HPLC grade solvents were purchased from VWR Scientific Co. (South Plainfield, N.J.).

Preparation of JS-K crystals was conducted according to the following procedures: NO gas was added to an argon-purged solution containing ethyl 1-piperazinecarboxylate (50.0 g, 0.316 mol), sodium methoxide (1.2 mol in methanol) and methanol (150 ml). The mixture was then stirred and purged with argon at ambient temperature for 48 h. The resulting solid was collected and washed with ethyl ether (2×100 ml) and then dried to constant weight at 25° C. to yield 37.6 g of an intermediate, sodium 1-(4-Ethoxycarbonylpiperazin-1-yl)diazen-1-ium-1,2-diolate. A solution of 2,4-dinitrofluorobenzene (25.8 g, 0.139 mol) in tert-Butyl alcohol (140 ml) was dropwise added to the intermediate in 5% aqueous $NaHCO_3$ (275 ml). The reaction mixture was stirred at ambient temperature for 18 h, and then extracted with $CH_2Cl_2$ (2×400 mL). The combined $CH_2Cl_2$ extracts were washed with HCl (2 M) and saturated aqueous $NaHCO_3$ (750 ml), dried over with $MgSO_4$. This material was washed with absolute ethanol (400 ml) to give partially purified product JS-K (48.5 g). Recrystallization was carried out by near dissolution of the JS-K in warm $CH_2Cl_2$ (300 ml), while stirring with ethanol (250 mL). The crystallized solid was collected and dried under vacuum at 35-40° C. for 10 h to give 37.5 g of purified JS-K. Its purity (>95%) was demonstrated by HPLC analysis.

1H-[1,2,4]oxadiazolo[4,3-a]quinoxalin-1-one (ODQ), daunorubicin, etoposide and bovine hemoglobin (Hb) were purchased from Sigma (St. Louis, Mo.). The impure component of methemoglobin was converted to Hb by addition of reducing agent sodium dithionite, which was later removed by dialysis (Martin et al., 1985—GET REFERENCE). ODQ has been demonstrated to be a selective inhibitor of sGC, which blocks the NO-sGC-cGMP pathway. ODQ was dissolved in dimethyl sulfoxide (DMSO) and made up to the final volume by addition of Krebs' solution.

All other chemicals were from Sigma (St. Louis, Mo.) unless otherwise noted.

Chromatography and Mass Spectrometry. High Performance Liquid Chromatography (HPLC) separations were carried out with a Phenomenex Luna 5 u C18(2) column (Torrance, Calif.) using a gradient of acetonitrile:water (each containing 0.1% formic acid) at a flow rate of 1 ml/min (% acetonitrile: 25% for 0-5 min followed by a linear program to 70% at 15 min).

HPLC-Mass Spectrometry (MS) studies were performed on an Agilent Capillary Series 1100 LC/MSD Ion Trap mass spectrometer with electrospray ionization in the positive ion mode (CITY, STATE). Separations were effected as above, except that the flow rate was 15 ul/min and the gradient was 10% acetonitrile for 0-5 min followed by a linear program to 70% at 15 min.

Molecular Modeling. 1-Chloro-2,4-dinitrobenzene (CDNB) is a model substrate used extensively for monitoring activity of glutathione S-transferase (GST) (Habig, W. H. (1974) Journal of Biochemistry 249: 7130-7139). GSTs with a higher specific activity toward CDNB appear to stabilize the Meisenheimer complex at the transition state better than the isoforms with poor catalytic activity for CDNB-GSH conjugation (Bico, P. et al. (1994) Biochem. Mol. Biol. Int. 33: 887-892). Crystal structures of a transition state analog, 1-(S-glutathionyl)-2,4,6-trinitrocyclohexadienate anion (GSTCD$^-$), in complex with rGSTM1-1, a Mu class rat GST isoform (Ji, X. et al. (1993) Biochemistry 32: 12949-12954), and with hGSTP1-1 (isoleucine-104, alanine-113 variant), a Pi class human GST isoform (Powell, M. J. D. (1977) Mathematical Progress 12: 241-254), have been reported and provided the foundation for modeling the transition state of GST-catalyzed GSH conjugation of JS-K.

The initial model of the Meisenheimer complex of GSH and JS-K was built based on the crystal structures of GSTCD$^-$ in rGSTM1-1 (Ji, X. et al. (1993) Biochemistry 32: 12949-12954) and that in hGSTP1-1 (Prade, L. et al. (1997) Structure 5: 1287-1295), respectively. The models were subject to geometry optimization using the conjugate gradient method of Powell (Powell, M. J. D. (1977) Mathematical Progress 12: 241-254) and docked into the active site of the model built based on the rGSTM1-1 (Ji, X. et al. (1993) Biochemistry 32: 12949-12954) and hGSTP1-1 (Prade, L. et al. (1997) Structure 5: 1287-1295) structures, respectively. The geometry of the protein-Meisenheimer complexes was then optimized and the energy was minimized (Powell, M. J. D. (1977) Mathematical Progress 12: 241-254).

Both complexes were built in dimeric form considering the fact that the biologically active forms of GSTs are dimeric proteins and that the glutathionyl moiety of GSH interacts with the side chains from both subunits (Armstrong, R. N. et al. (1994) Adv. Enzymol. Relat. Areas Mol. Biol. 69: 1-44; Wilce, M. C. J. et al. (1994) Biochim. Biophys. Acta 1205: 1-18; Dirr, H. et al. (1994). Eur. J. Biochem. 220: 645-661; Armstrong, R. N. et al. (1997) Chem. Res. Toxicol. 10: 2-18). The Engh and Huber (Engh, R. A. et al. (1991). Acta Crystallogr. 47: 392-400) geometric parameters were used as the basis of the force field. No crystal structure of Alpha class GST-bound GSTCD$^-$ is available. The Meisenheimer complex for Alpha class GST was therefore built by modifying those for rGSTM1-1 and hGSTP1-1 based on the structures of hGSTA1-bound S-benzyl-GSH (Sinning, I., et al. (1993) J. Mol. Biol. 232: 192-212) and the GSH conjugate of ethacrynic acid (Cameron, A. D. et al. (1995) Structure 3: 717-727). After energy minimization, the Meisenheimer complex for hGSTA1-1 was docked in the active center of the enzyme and the protein-Meisenheimer complex was subject to energy minimization as described above. (Jones, T. A. et al. (1997) Methods Enzymol. 277: 173-208) and X-PLOR (Brünger, A. T. et al. (1997) Methods Enzymol. 277: 243-269).

Determination of Specific Activity of Human GSTs Toward JS-K. Purified preparations of recombinant hGSTA1-1, hGSTM1-1 and hGSTP1-1 were obtained from Panvera (Madison, Wis.). The activity of human GST toward CDNB was determined, as described by Habig et al. (Habig, W. H. et al. (1974) J. Biol. Chem. 249: 7130-7139), prior to activity measurements with JS-K to ensure that the enzyme preparations were catalytically active. For activity measurement toward JS-K, the reaction mixture in a final volume of 1 ml contained 100 mM potassium phosphate buffer (pH 6.5), 1 mM GSH, 0.045 mM JS-K, and an appropriate amount of human GST isoenzyme protein. The reaction was started by the addition of JS-K, and the rate of reaction was monitored by measuring decrease in absorbance of JS-K at 298 nm due to its utilization during reaction with GSH. The specific activity toward JS-K was calculated using an extinction coefficient of 18 mM$^{-1}$ cm$^{-1}$ at 298 nm.

Measurement of NO Release. Chemiluminescence detection and quantification of NO evolving from the reactions of JS-K were conducted using an NO-specific Thermal Energy Analyzer (Model 502A, Thermedics, Analytical Instrument Division, Waltham, Mass.) essentially as previously described (Keefer, L. K. et al. (1996) Methods Enzymol. 268: 281-293). Briefly, pH 7.4 phosphate buffer containing 1 mM GSH was sparged with inert gas until a steady detector response was established. Where indicated, GSTs were added to a final concentration of 1.67 ug of enzyme/ml. The NO release profile was followed at 37° C. for 45 min after injecting JS-K at a final concentration of 133 nM to start the reaction. The resulting curve was integrated to quantify the amount of NO released/mole of compound.

Cell Lines and Culture Conditions. HL-60, DLD1, and U937 cells were obtained from ATCC (Rockville, Md.). Meth A cells were from Dr. Wolfram Samlowski (University of Utah, Salt Lake City, Utah). The PPC-1 cell line was provided by Dr. Graeme Bolger (University of Alabama, Birmingham, Ala.). For the cell growth and apoptosis experiments, cells were cultured at a density of 150,000 cells/ml in RPMI-1640 with 10% fetal bovine serum at 37° C. in a 5% $CO_2$ humidified atmosphere. Agents were added at the indicated concentrations 24 h after culture initiation. At the indicated time intervals, cells were harvested and washed twice in phosphate buffered saline (PBS) prior to processing for analysis of growth, differentiation, and apoptosis.

Cell Growth, Differentiation and Apoptosis Assays. The number of viable cells was determined using the MTT assay according to the manufacturer's protocol (Promega, Madison, Wis.) or using a Coulter counter. Briefly, a MTT assay is an analytical technique that uses the dye dimethylthiazolyl-diphenyltetrazolium (MTT) which turns from yellow to brownish-purple as it is reduced in the mitochondria of living cells. The assay is useful in calorimetric quantitation of cell viability and proliferation. In contrast, cell differentiation was evaluated using Wright and Non-Specific Esterase (NSE) staining of cells collected on microscope slides by cytospin as previously described (Magrinat, G. et al. (1992) Blood 80: 1880-1884). Apoptosis was assayed by flow cytometry and by determining DNA fragmentation using agarose gel electrophoresis as previously described (Shami, P. J. et al. (1998) Leukemia 12: 1461-1466). For the flow cytometry assay, we used the propidium iodide staining method of Nicoletti et al. (Nicoletti, I. et al. (1991) J. Immunol. Methods 139: 271-279).

In vivo Studies of JS-K. NOD/SCID (non-obese diabetic-severe combined immune deficient) mice were bred and maintained at the Huntsman Cancer Institute at the University of Utah (Salt Lake City, Utah). Experiments were performed on male or female mice 6-8 weeks of age at the Animal Care Facility of the SLC VA Medical Center after approval by the Institutional Animal Care and Use Committees. Systolic blood pressure was measured on unanesthetized NOD/SCID mice using an occluding tail cuff and a pulse transducer connected to a blood pressure transducer/monitor from World Precision Instruments (Sarasota, Fla.). Signals from the blood pressure monitor and pulse transducer were transmitted to a Stoelting MacLab2 data acquisition device (Wood Dale, Ill.) that feeds directly into a Macintosh computer. The recorded data were analyzed using the Stoelting Chart data analysis software. Measurements were done in triplicate at each time point.

To study the in vivo antineoplastic potency of JS-K, NOD/SCID mice were injected in the flanks subcutaneously with HL-60 or PPC-1 cells ($2.5 \times 10^6$ cells per flank). When subcutaneous tumors were palpable, treatment with JS-K or an equal volume of vehicle (20% dimethyl sulfoxide in PBS) was started using the indicated doses and route. Tumor size was measured daily or every other day using a Vernier caliper. Tumor volume was calculated using the formula: width×length×[(width+length)/2]×0.5236. Fifteen to 20 days after tumor cell implantation, animals were sacrificed by $CO_2$ inhalation and tumors were collected for histochemical analysis.

Histological Analysis of Tumors. After sacrifice, subcutaneous tumors were dissected out, fixed in 10% formaldehyde and imbedded in paraffin. Four-um sections were cut and stained with Hematoxylin and Eosin.

Preparation of Rabbit Aortic Rings for Bioassay of NO Activity. The preparation of rabbit aortic rings was similar to that described previously (Jia L and Furchgott R F (1993) *J Pharmnacol Exp Ther* 267: 371-378.), and the animal protocol was approved by the Institutional Animal Care and Use Committee. Briefly, a male New Zealand rabbit was anesthetized by an intravenous injection of sodium pentobarbital into a marginal ear vein. The descending thoracic aorta was quickly removed. The aortic rings (2 mm in length) were prepared and mounted in 20 ml of Krebs' solution (bubbled with 95% $O_2$/5% $CO_2$, 37° C.) in organ chambers. Tension was measured isometrically, using Grass FTO3C transducers, and displayed on model 7 Grass polygraphs. Rings were allowed to equilibrate for at least 90 min before experiments were initiated. Basal tension was maintained at approximately 3 g. To allow studies on relaxation, each ring was precontracted submaximally by addition of 50-100 nM phenylephine to the bathing solution. When the contraction had reached a steady state, JS-K was added successively to the bathing solution until the maximal relaxation was obtained. Hb and ODQ were also added to the bathing solution to investigate the mechanisms of action of JS-K.

Anticancer screen of JS-K against the NCI 58 human cancer cell lines. Cells initially maintained in multiple T150 tissue-culture flasks were detached from the flasks by addition of 2-3 ml of 0.05% trypsin-EDTA when cells reached 70-90% confluency. Thereafter, trypsin was inactivated by addition of 10 ml of RPMI 1640 medium containing 5% fetal bovine serum. All cells were then transferred and seeded onto 96-well microtiter plates at densities between 5,000 and 30,000 cells per well. Three cell lines were inoculated per plate. The cells were grown in RPMI 1640 supplemented with 5% fetal bovine serum and 2 mM L-glutamine for 24 h at 37° C. to allow stabilization prior to addition of JS-K. A total of 58 human cancer cell lines were used for the broad screening. The stock solution of JS-K in DMSO was serially diluted with the RPMI 1640 medium and added immediately to the microtiter plates to produce five concentrations of JS-K, i.e., $10^{-4}$, $10^{-5}$, $10^{-6}$, $10^{-7}$ and $10^{-8}$ M. JS-K was incubated with cells for 48 h.

At the end of incubation, the cells were fixed in situ by 10% trichloroacetic acid, and washed five times with water and dried. Sulforhodamine B (0.4% in 1% acetic acid), a protein stain binding to basic amino acids of cellular macromolecules, was added to each well, and incubated for 10 min at room temperature. Unbound Sulforhodamine B is removed by washing five times with acetic acid. Then the plates were air-dried. Bound stain is solubilized with Tris buffer, and the optical densities were read at 515 nm. The optical densities generated from Sulforhodamine B staining are a function of cell mass and growth rate (Monks et al., 1991). Thus cells with small mass (e.g., leukemias) or relatively slow division rate (e.g., renal RXF393 and lung cancer HOP-92) were inoculated at the relatively high densities of 20,000-30,000 cells per well, while more rapidly dividing cells (e.g., colon HT29 and HCT-116 cell lines, and lung NCI-H460 cells) were inoculated at 5,000 cells per well. For the suspended leukemia cell subpanel, the cells were fixed to the bottom of the microtiter well by adding cold trichloroacetic acid (final concentration 16%) at the end of the drug-incubation period.

The dose-response curve is created by plotting the % growth against the $\log_{10}$ of the corresponding JS-K concentrations for each cell line by disease subpanel group. Three horizontal lines are provided at the % growth values of 50, 0 and −50, respectively. Thus the molar JS-K concentrations corresponding to points where the curves cross these lines represent the interpolated values that cause 50% growth inhibition ($GI_{50}$, the JS-K concentration causing a 50% reduction in the net protein increase in control cells), total growth inhibition (TGI, the JS-K concentration causing amount of protein at the end of incubation to be equal to the amount at the beginning) and 50% cell killing ($LC_{50}$, the JS-K concentration causing a 50% reduction in the protein of treated cells at the end of the drug incubation, compared with that at the beginning, indicating a net loss of cells following drug treatment), respectively.

Combination treatment. For combined drug treatment, HL-60 cell lines were pretreated with JS-K (0.25 µM) for 6 h in RPMI 1640 at 37° C. The JS-K-containing culture medium was then removed and replaced with fresh RPMI-1640. Three different concentrations of either etoposide (0.2, 0.3 and 0.4 µM) or daunorubicin (5, 10 and 50 nM) were added to the pretreated HL-60 cells. The cells were incubated at 37° C. for additional 48 hours. Solution of 3-[4,5-dimethylthiazol-2-yl]-2,5-diphenyltetrasodium bromide (MTT) tetrazolium salt (1 mg/ml) was added to the cells. The cells were incubated again for 3 h to allow for MTT metabolism to formazan by the succinate-tetrazolim reductase system active only in viable cells. A solution of 0.04 N HCl in isopropyl alcohol was added to stop the MTT assay. The supernatant was then aspirated and 150 µl of trituration was added to dissolve the water-insoluble blue formazan. The optical densities were read on a spectrophotometric plate reader at a single wavelength of 570 nm. The absorbance for control cells was defined as an MTT activity of 100%.

Calculations and Statistical Analysis. Results are expressed as averages of multiple experiments with standard error of the mean (SEM). SEM was calculated as the standard deviation of different measurements divided by the square root of the number of measurements. Differences were considered statistically significant if the P value was below 0.05 as calculated using the t-test.

Example One

Glutathione S-Transferase Activated NO Donors and Leukemia Cell Growth

A library of approximately 50 compounds from a family of $O^2$-aryl diazeniumdiolate NO donors that are inactive in the pro-drug form were screened for in vitro and in vivo antileukemic activity. For the initial screen, HL60 cells were cultured in triplicate in RPMI1640/10% FBS under standard conditions. Compounds were added to the cultures at the following concentrations: 0, 0.1, 1, 10, and 100 micromolar (uM). Three days after addition of the compounds cell growth was determined either using a Coulter counter or using the MTT assay. Compounds that had a 50% growth inhibitory concentration (IC50) greater than 10 uM were not subjected to further screening. Compounds with IC50's below 10 uM were used for further in vitro and in vivo screens.

A range of inhibitory concentrations ($IC_{50}$) were found ranging from the millimolar to the submicromolar level. The most active compound of this family appeared to be $O^2$-(2,4-dinitrophenyl)1-[(4-ethoxycarbonyl)piperazin-1-yl]diazen-1-ium-1,2-diolate, also known as JS-K. This molecule appeared to have an ($IC_{50}$) at three days of 0.22 uM. Two additional compounds were also good inhibitors of cell growth. They were is $O^2$-(2,4-dinitrophenyl) 1-[4-phenylpiperazin-1-yl]diazen-1-ium-1,2-diolate (JXC-2-40) and $O^2$-(2,4-dinitrophenyl) 1-[4-pyrimidin-2-yl]diazen-1-ium-1,2-diolate (JXC-2-56). JS-K was used in the studies described in the following Examples.

Example Two

Inhibition of Leukemia Cell Growth

The antiproliferative effects in the human AML (Acute Myeloid Leukemia) cell lines, HL-60 (myeloid leukemia) and U937 (monoblastic leukemia) cells were treated with JS-K for a period of 3 days, upon which cell growth was evaluated using a Coulter counter (CITY, STATE). JS-K was added to HL-60 cells at 0, 0.25, 0.5, 0.75, and 1.0 µM concentrations. JS-K appeared to be a very potent in vitro growth inhibitor of leukemia calls with $IC_{50}$ values of 0.22 and 0.33 µM for HL-60 and U937 cells, respectively. These data are the mean of 3 separate studies. JS-K demonstrated an inhibitor effect on leukemia cell growth. Similar results were obtained in U937 cells under similar conditions.

Example Three

Induction of Apoptosis in Leukemia Cells

To determine if JS-K could induce apoptosis in leukemia cells, it was added to HL-60 cells at concentrations of 0.5 and 1.0 µM. Three days post-addition, the percentage of apoptotic cells was determined by measuring the number of cells in the sub-$G_0$ fraction of the cell cycle using flow cytometry. Based on a mean of 3 different studies, JS-K appeared to increase the number of apoptotic cells from 7 percent to 27±3 and 43±2 percent at 0.5 and 1.0 µM, respectively. Therefore, JS-K is a potent inducer of apoptosis in HL-60 cells, and appears to act in a dose-dependent manner (data not shown).

These results were confirmed using DNA laddering assays: JS-K was added to HL-60 cells at a concentration of 1 µM. Twenty-four hours post-addition, apoptosis induction was assayed by DNA laddering. The results confirmed that JS-K is a potent inducer of apoptosis in leukemia cells.

Example 4

Activation of JS-K by Leukemia Cells to Generate NO

To show that JS-K is activated by leukemia cells to generate NO, the compound was added to HL-60 cells in serum-free buffer. Production of NO was then determined by measuring levels of nitrate and nitrite, byproducts of NO oxidation. Serum-free buffer was used to eliminate the confounding effects of nitrates in the serum or medium. When added to HL-60 cells suspended in serum-free phosphate buffered saline (PBS) buffer at a concentration of 10 µM, JS-K appeared to generate NO in a time-dependent fashion with peak levels at 24 hours. Supernatants from HL-60 cells did not induce activation of JS-K and NO release, suggesting a mechanism of intracellular activation of the compound. This was confirmed by results indicating that NO generation by JS-K was positively correlated to the number of leukemia cells in culture. For this, JS-K was added to HL-60 cells suspended in serum-free PBS at a concentration of 20 µM and nitrate+nitrite levels in the supernatants were determined 24 hours post-addition. The extent of NO release was positively correlated with the cell number thus indicating that the compound is activated by the leukemia cells intracellularly to generate NO in a dose-dependent fashion (results not shown).

Example 5

The Effect of JSK on Blood Pressure

Because of the known effects of NO on blood pressure, it was important to show that JS-K does not induce hypotension prior to performing any in vivo therapeutic experiments. A dose escalation study was performed where JS-K was administered intravenously to NOD/SCID mice and measurements of systolic blood pressure on the awake, unanesthetized animals were taken periodically, up to 275 minutes after administration, using a tail cuff. At doses of up to 4 µmol/kg of JS-K (a dose that would achieve a peak blood concentration of approximately 68 µM which is far above its $IC_{50}$ for HL-60 cells), JS-K did not appear to induce any significant hypotension (data not shown).

Example 6

In-Vivo Effect on Leukemia Cell Implant Growth after Introduction

To determine the in vivo therapeutic efficacy of JS-K, NOD/SCID mice were injected subcutaneously with $5 \times 10^6$ HL-60 cells in the flanks. When tumors were measurable (4 to 5 days after leukemia cell inoculation), the mice were divided into 2 groups that received either vehicle or JS-K at a dose of 4 µmol/kg administered intravenously 3 times per week. After seventeen days from the leukemia cell inoculation there appeared to be a significant difference in tumor volume between vehicle and JS-K treated animals: tumor volume was 9.51±1.22 and 4.15±1.06 cm$^3$ in vehicle and JS-K treated animals, respectively. Thus JS-K is believed to be responsible for a significant delay in leukemia implant growth in vivo. Histologic sections of the tumors at the time of experiment termination indicated extensive necrosis in implants obtained from JS-K treated animals and not in implants obtained from vehicle-treated mice.

Sixteen days after starting therapy the average tumor volumes in control and JS-K treated mice were 8.34±0.72 and 3.13±1.14 cm$^3$ (P=0.039), respectively, reflecting a more than 50% reduction in tumor volume in treated mice. Histological analysis of HL-60 cell tumors obtained from vehicle-treated mice indicated a uniform population of densely packed myeloblasts. The cells appeared to be highly invasive, penetrating the surrounding muscles and showing high mitotic activity. The degree of necrosis appeared to be minimal. On the other hand, histologic analysis indicated extensive (>50%) cell necrosis in HL-60 cell tumors obtained from the JS-K-treated mice as compared to ~10% in controls.

A second experiment was conducted with NOD/SCID mice injected intravenously with HL-60 cells. Control mice appeared to develop systemic disease as evidenced by large abdominal lymph nodes and leukemia cell engraftment in the liver, spleen and bone marrow. Treated mice were administered 1 µmol/kg intravenous JS-K for three to four weeks beginning one day after inoculation. Control mice were treated with vehicle. A human-specific anti-CD15 antibody was utilized in flow cytometric analysis to identify the leukemic cells. The JS-K-treated inoculated mice appeared to have decreased leukemic cell engraftment in the bone marrow and liver when compared to controls. Additionally, the number and size of enlarged abdominal lymph nodes appeared to be smaller in these animals. Two of the five treated JS-K-treated mice indicated almost no evidence of disease three to four weeks after inoculation. Collection and culture of bone marrow from JS-K-treated and control mice with human hematopoietic cell-selective semi-solid medium appeared to produce few if any colonies of cancerous cells in JS-K-treated mice.

Example Seven

Effect of JS-K on Prostate Cancer Cells

To determine if JS-K is cytotoxic to solid tumors, the effect of JS-K on the in vitro and in vivo growth of the prostate cancer cell line PPC-1 was studied. Similar to studies in HL-60 cells, indications are that JS-K appears to be a potent growth inhibitor for prostate cancer cells in vitro and in vivo. For the in vitro experiments, JS-K was added to PPC-1 cells at 1, 2, 3, 4, and 5 µM concentrations. Cell growth was measured 3 days after addition of the NO donor and at each concentration of JS-K it appeared to be a potent inhibitor of prostate cancer growth. For the in vivo experiments, NOD/

SCID mice were inoculated subcutaneously with 5×10$^6$ PPC-1 cells, as described above. When the subcutaneous tumors were measurable, JS-K was administered intravenously at a dose of 4 µmol/kg or an equal volume of vehicle 3 times per week. JS-K appeared to induce a significant delay in prostate cancer growth in vivo. Histologic sections of the tumors at the time of experiment termination indicated extensive necrosis in implants from animals treated with JS-K.

In order to determine whether JS-K inhibits the in vivo growth of solid tumor cells, NOD/SCID mice were implanted with 2.5×10$^6$ PPC-1 (prostate carcinoma) cells and treated with 4 µmol/kg JS-K or an equal volume of vehicle intravenously 3 times a week. Similar to the observation with HL-60 cells, JS-K treatment appeared to inhibit the growth of PPC-1 cells in vivo. Nineteen days after start of therapy, subcutaneous tumor implant volumes were 0.368±0.082 and 0.107±0.053 cm$^3$ (P=0.0073) in vehicle and JS-K-treated animals, respectively. Similar to HL-60 cells, PPC-1 cells were highly aggressive and invaded the surrounding tissues. Histologic analysis indicated a high degree of extensive tumor necrosis in implants obtained from JS-K-treated animals.

Example 8

Reactivity of JS-K with GSH

The diazeniumdiolate ion appears to resemble chloride as a leaving group in $S_NAr$ reactions (Saavedra, J. E. et al. (2001) J. Org. Chem. 66: 3090-3098). Since 1-chloro-2,4-dinitrobenzene is believed to react with GSH, it was anticipated that JS-K would be similarly converted to DNP-SG. This was indicated by HPLC-MS where there appeared to be an 85% conversion of JS-K to DNP-SG within a 30-min incubation period at 37° C. in pH 7.4 phosphate buffer. Similar results appeared in a RPMI-1640 cell culture medium. Pseudo-first order kinetic plots for the reaction of GSH with JS-K in 0.1 M phosphate buffer (pH 7.4) were obtained with GSH (1-5 mM) in large excess of the substrate. Excellent first-order behavior was observed over several half-lives, and measured first-order rate constants appeared to show a linear dependence on [GSH]. The slope and y-intercept of the line yielded values for the second-order $[k_2=(1.02\pm0.04)$ M$^{-1}$ s$^{-1}]$ and first order $[k_1=(4\pm12)\times10^{-5}$ s$^{-1}]$ rate constants for the reactions of JS-K with GSH and water, respectively, at 37° C. in 0.1 M phosphate buffer, pH 7.4. The ultraviolet spectral changes accompanying the reaction in a second cell culture medium (Dulbecco's Modified Eagle's Medium) appeared to confirm the above stated kinetic rate constants.

Example 9

Hydrolysis of JS-K

JS-K appeared to be resistant to simple hydrolysis under these conditions, as reflected in the near-zero y intercept. For increased JS-K consumption rate at an initial concentration of 50 uM in 0.1 M phosphate (pH=7.4) at 37° C. as a function of increasing GSH concentration. The value of $k_1$ obtained from the intercept appeared to be in statistical agreement with the rate constant for JS-K hydrolysis ($1\times10^{-6}$ s$^{-1}$) measured separately in the absence of GSH. The small amount of the hydrolysis product (2,4-dinitrophenol) (data not shown) was apparently formed in the dimethyl sulfoxide stock solution, which in this case had been stored in the refrigerator with intermittent use during several weeks. Hydrolysis was much more facile at pH=12, which was expected for a compound type designed to be activated for NO release by nucleophilic attack.

Example 10

Catalysis of the GSH/JS-K Reaction and NO Release by GST

The reaction of GSH with CDNB is believed to be catalyzed by several classes of human GSTs, and thus this electrophilic substrate is often used for quantifying their activity. Given the similarity of diazeniumdiolate ions to chloride as a leaving group in $S_NAr$ reactions (Saavedra, J. E. et al. (2001) J. Org. Chem. 66: 3090-3098), JS-K is also expected to undergo GST-catalyzed conjugation with GSH. To gain insights into the effect the obvious steric differences between chloride and the diazeniumdiolate ion, we modeled the accommodation of the Meisenheimer complex of JS-K in the active sites of the three major classes of human GSTs, i. e., hGSTA1-1, hGSTM1-1, and hGSTP1-1. Both hGSTA1-1 and hGSTM1-1 classes of GSTs appeared to accommodate the Meisenheimer complex very well, but hGSTP1-1 appears to have serious steric conflicts with the diazeniumdiolate moiety of the transition state complex (data not shown). Based on molecular modeling, it was predicted that hGSTA1-1 and hGSTM1-1 would be more effective than hGSTP1-1 for catalyzing the GSH conjugation of JS-K.

These predictions appeared to be confirmed by determining the activities of recombinant hGSTA1-1, hGSTM1-1, and hGSTP1-1 preparations toward JS-K. Specific activities of GSTs toward CDNB were determined prior to activity measurement with JS-K to ensure that the enzyme preparations were catalytically active. The specific activities of the GSTs toward CDNB were comparable to the values published in the literature (Hayes, J. D. et al. (1995) Crit. Rev. Biochem. Mol. Biol. 30: 445-600). In agreement with our prediction, hGSTP1-1 appeared to be much less active than hGSTA1-1 or hGSTM1-1 for GSH conjugation of JS-K.

These reactions led to NO generation as predicted as indicated by purging gases from the solution as they formed into an NO-specific chemiluminescence detector. Consistent with JS-K's resistance to hydrolysis and its reactivity toward GSH, as noted above, NO did not appear to be detected until 1 mM GSH was added to the pH 7.4 phosphate/0.67 uM JS-K solution. In the absence of enzyme, NO release began immediately upon adding GSH, increasing in rate until plateauing at 8 min and integrating to a total of 1.1 mol of NO per mol of JS-K within 43 min of mixing. It is believed that the hGSTP1-1 isoform catalyzed this reaction, but only weakly; that this was not due to a deleterious effect of JS-K exposure on the enzyme's activity was demonstrated in its unfettered ability, in the presence of up to 80 uM JS-K, to catalyze CDNB's conjugation with GSH. The performance of hGSTA1-1 and hGSTM1-1 isoforms indicated that they were much superior to hGSTP1-1 as catalysts for JS-K conjugation. NO release appears to be consistent with the conclusion from the JS-K consumption studies that suggested JS-K is metabolized much better by hGSTA1-1 and hGSTM1-1 than by hGSTP1-1.

Example 11

Growth Inhibitory Properties of JS-K

A comparison between the growth inhibitory ability of JS-K and those of the chemotherapeutic agents daunorubicin and etoposide in a HL-60 assay system indicates that pretreatment of cells with JS-K prior to administration of either of the two chemotherapeutic agents has an additive effect. The $IC_{50}$s of JS-K, daunorubicin, and etoposide were 0.5, 0.01, and 0.3 uM, respectively, demonstrating synergy and an additive effect. 1-Chloro-2,4-dinitrobenzene, a compound with the same aryl ring as JS-K that does not release NO, inhibited the in vitro growth of HL-60 cells but at much higher concentrations, with an $IC_{50}$ estimated at 6.7 uM. JS-K also appeared to inhibit the growth of U937 (monocytic leukemia) cells with an $IC_{50}$ of 0.3 uM. There were also indications that solid tumor cell growth was also inhibited by JS-K, although to a lesser extent than leukemia cells; the $IC_{50}$s for the three lines tested, PPC-1, DLD-1, and Meth A, appeared to be an order of magnitude greater than those for the two leukemia lines.

In order to determine whether modulation of the GST pathway affects JS-K's antineoplastic properties, studies were performed using N-acetyl-L-cysteine (NAC) or buthionine sulfoximine (BSO). NAC increases intracellular GSH levels while BSO inhibits its synthesis (Anderson, M. E. (1998). Chem. Biol. Interact. 111-112: 1-14). Treatment of HL-60 cells with NAC (0.3-0.5 mM) or BSO (0.2-0.3 mM) did not appear to significantly affect cell growth. Studies suggested that pretreatment of the cells for 2-6 h with NAC prevented the JS-K-induced growth inhibition. Pretreatment of HL-60 cells with BSO for 2-6 h did not appear to prevent the JS-K-induced growth inhibition, while pretreatment of the cells with BSO for 24 h appeared to enhance the effects.

Example 12

JS-K Induction of Apoptosis

In order to determine if JS-K was inducing apoptosis by a caspase dependent mechanism, the pan-caspase inhibitor C-VAD-FMK was added to HL-60 cells in combination with JS-K. Three days later the cells were measured using the MTT assay. It appeared that 50 uM C-VAD-FMK increased cell growth to 116+/−2.2% of untreated control cells (p<0.0005). Conversely, it appeared that cells treated with 0.75 uM JS-K had a growth of 28+/−0.79% of untreated control cells. When HL-60 cells were treated with both C-VAD-FMK and JS-K at the same concentrations, cell growth appears to be restored to 79+/−2.4% of untreated control cells (p<0.0005).

The number of apoptotic cells was then determined by flow cytometry. Results indicated that treatment of cells with 50 uM C-VAD-FMK decreased the number of apoptotic cells from 1.5+/−1.4% to 32.8+/−0.49% (p=000.1). Co-administration of both C-VAD-FMK and JS-K at the same concentration appeared to restore the percentage of apoptotic cells to 2.65+/−0.28% (p=0.44 when compared to untreated controls).

JS-K appears to be inducing apoptosis and inhibiting growth by a caspase dependent mechanism.

Example 13

Effect of JS-K on Leukemia Cell Differentiation

HL-60 cells were treated with JS-K at a concentration of 0.5 uM for 3-5 days. Wright stain appeared to reveal morphologic changes consistent with a monocytic phenotype, namely development of folded nuclei, large cytoplasms, and cytoplasmic vacuoles. Non-specific esterase staining (NSE, an enzyme specific to the monocytic lineage) indicated that JS-K increased the percentage of HL-60 cells expressing NSE from 1 to 40%. JS-K appears to induce cell differentiation.

Example 14

JS-K Exerts a Dose-Dependent Vasorelaxation Effect

The ability of JS-K to function as a NO donor was examined in the rabbit thoracic aorta model. This is a standard tool used for the discovery and identification of NO activity and simulates the endothelial NO effects, as well as ascertains the ability of a particular compound to be a NO donor. JS-K exhibited a dose-dependent vasorelaxation that reached a maximum at 100 nM. The vasoactivity was reversible in the presence of a NO scavenger and a specific inhibitor of the NO-sGC-cGMP pathway, indicating that JS-K possesses potent NO bioactivity and also delivers NO in a controlled manner.

Example 15

JS-K Exhibits Dose-Dependent Inhibition of Cancer Cells

The ability of JS-K to inhibit cell growth was determined in a standard high-flux anticancer drug screen (Monga M. and Sausville E. A. (2002). Leukemia 16(4) 520-6). JS-K produced dose-dependent growth inhibition of all 9 cancer subpanels of 58 human cell lines with mean $GI_{50}$, TGI, and $LC_{50}$ values of 1.3, 6.6 and 29.5 µM, respectively. HL-60 leukemia cells appeared to be the most sensitive to the cytostatic and cytotoxic effects of JS-K, followed by renal 786-0, ACHN and CAKI-1 cells, melanoma M14 cells and colon HCT-15 cells. The renal cancer subpanel appeared to be the most sensitive to JS-K, followed by the ovarian cancer, non-small cell lung cancer and CNS cancer subpanels. Although the colon, melanoma, and breast cancer subpanels showed good sensitivity to JS-K, some cell lines within those subpanels exhibited $LC_{50}$s more than 100 µM. JS-K also displayed moderate inhibition against prostate cancer cell lines.

Example 15

JS-K Exhibits Dose-Dependent Inhibition of Cancer Cells

Pretreatment of HL-60 cells with JS-K (0.25 µM) significantly enhanced efficacy of daunorubicin and etoposide on the HL-60 cells (data not shown).

Example 16

JS-K Exhibits Dose-Dependent Inhibition of Bacteria, Viruses, Fungi and Parasites An individual with a bacterial, viral, fungal or parasitic infection is administered a therapeutically effective amount of JS-K to treat such infection. Administration of JS-K causes elimination of such infection.

All of the COMPOSITIONS, METHODS and APPARATUS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPA- RATUS and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

I claim:

1. A method for treating cancer in a human comprising
   (a) identifying a human having cancer selected from the group consisting of prostate, renal, melanoma, colon, ovarian, lung, and central nervous system cancer; and
   (b) administering to the human $O^2$-(2,4-dinitrophenyl) 1-[(4-ethoxycarbonyl)piperazin-1-yl]diazen-1-ium-1,2-diolate (JS-K).

2. The method of claim 1, wherein JS-K induces apoptosis of cancer cells in the human.

3. The method of claim 1, wherein the administration of JS-K does not induce hypotension in the human.

4. The method of claim 1, further comprising administration of a chemotherapeutic agent, radiation, or a combination thereof in conjunction with JS-K.

5. The method of claim 4, wherein said chemotherapeutic agent is selected from the group consisting of 5-fluorouracil (5FU); etoposide (VP-16); actinomycin-D; mitomycin C; cisplatin (CDDP); doxorubicin; a podophyllotoxin; a DNA alkylating agent, or a camptothecin; and a combination of any of the above.

6. The method of claim 4, wherein the radiation is X-rays, y-radiation, UV-radiation, microwaves, or electronic emissions.

7. The method of claim 4, wherein JS-K and the chemotherapeutic agent and/or radiation are administered simultaneously or sequentially to the subject.

8. A method of killing a target cancer cell in a human comprising
   (a) identifying a human having cancer selected from the group consisting of prostate, renal, melanoma, colon, ovarian, lung, and central nervous system-cancer; and
   (b) administering to the human $O^2$-(2,4-dinitrophenyl) 1-[(4-ethoxycarbonyl)piperazin-1-yl]diazen-1-ium-1,2-diolate (JS-K).

9. The method of claim 8, wherein JSK is administered with a DNA damaging agent.

10. The method of claim 8, wherein JS-K induces apoptosis of cancer cells in the human.

11. The method of claim 8, wherein the administration of JS-K does not induce hypotension in the human.

12. The method of claim 8, further comprising administration of a chemotherapeutic agent, radiation, or a combination thereof in conjunction with JS-K.

13. The method of claim 12, wherein said chemotherapeutic agent is selected from the group consisting of 5-fluorouracil (5FU); etoposide (VP-16); actinomycin-D; mitomycin C; cisplatin (CDDP); doxorubicin; a podophyllotoxin; a DNA alkylating agent, or a camptothecin; and a combination of any of the above.

14. The method of claim 12, wherein the radiation is X-rays, y-radiation, UV-radiation, microwaves, or electronic emissions.

15. The method of claim 12, wherein JS-K and the chemotherapeutic agent and/or radiation are administered simultaneously or sequentially to the subject.

16. The method of claim 8, wherein JSK is administered with a DNA damaging agent.

* * * * *

UNITED STATES PATENT AND TRADEMARK OFFICE
CERTIFICATE OF CORRECTION

| | | |
|---|---|---|
| PATENT NO. | : 8,404,665 B2 | Page 1 of 1 |
| APPLICATION NO. | : 10/508744 | |
| DATED | : March 26, 2013 | |
| INVENTOR(S) | : Paul Shami | |

It is certified that error appears in the above-identified patent and that said Letters Patent is hereby corrected as shown below:

In the specification

Please replace the paragraph at column 1, lines 14-16 with the following paragraph:

This invention was made with government support under Grant Number CA129611 awarded by the National Institutes of Health. The government has certain rights in the invention.

Signed and Sealed this
Nineteenth Day of April, 2016

Michelle K. Lee
*Director of the United States Patent and Trademark Office*